United States Patent [19]

Maries et al.

[11] 4,336,153

[45] Jun. 22, 1982

[54] GLASS COMPOSITION FOR WATER SETTING ION-POLYMER CEMENTS

[75] Inventors: Alan Maries, London; Francesca M. Shreeve, Harlow, both of England

[73] Assignee: International Standard Electric Corporation, New York, N.Y.

[21] Appl. No.: 197,404

[22] Filed: Oct. 16, 1980

Related U.S. Application Data

[62] Division of Ser. No. 110,056, Jan. 7, 1980, Pat. No. 4,250,277.

[30] Foreign Application Priority Data

Jan. 9, 1979 [GB] United Kingdom ................ 7900813

[51] Int. Cl.$^3$ .......................... C08K 3/00; C08K 3/38; C08K 3/10
[52] U.S. Cl. ....................................... 252/182; 106/35; 106/104; 106/286.5; 106/287.17; 260/998.11; 525/328; 525/329; 525/337
[58] Field of Search ................. 252/182; 106/35, 104, 106/286.5, 287.17; 260/42.52, 998.11; 525/328, 337, 329

[56] References Cited

U.S. PATENT DOCUMENTS

| | | | |
|---|---|---|---|
| 3,826,778 | 7/1974 | Dietz | 260/998.11 |
| 3,873,327 | 3/1975 | Duff | 260/998.11 |
| 3,882,080 | 5/1975 | Schmitt et al. | 260/998.11 |
| 3,971,754 | 7/1976 | Jurecic | 260/998.11 |

*Primary Examiner*—Irwin Gluck
*Attorney, Agent, or Firm*—James B. Raden; Harold J. Holt

[57] ABSTRACT

A glass composition for effecting crosslinking of a polycarboxylic acid cement and cement compositions formed therefrom. The glass is of the aluminoborate type and comprises 40 to 75 mole % boric oxide, not more than 60 mole % zinc oxide, not more than 50 mole % calcium oxide and not more than 20 mole % alumina. Cements formed from the glasses have a wide range of applications including structural cements, dental filler and orthopaedic cements.

7 Claims, No Drawings

GLASS COMPOSITION FOR WATER SETTING ION-POLYMER CEMENTS

This is a division of application Ser. No. 110,056, filed Jan. 7, 1980, now U.S. Pat. No. 4,250,277.

This invention relates to glass compositions such as are employed in the preparation of polycarboxylic acid water setting cements and to cement composition incorporating such glasses.

It is well known that polycarboxylic acid materials, such as polyacrylic acid, can be crosslinked to form a solid cement by treatment with divalent or polyvalent metal ions. Typically the metal ion comprises zinc or calcium. Recent work has shown that the metal ions required for crosslinking such cements may be supplied from glass compositions which may or may not completely dissolve in water as the cement sets. Glass compositions of this type are described in our co-pending British applications No. 23789/77 (C. F. Drake 59), No. 48193/77 (C. F. Drake 62) and No. 43601/78 (C. F. Drake—N. R. Adams 66-1) and pending British application No. 50578/76 (Smith and Nephew).

Two stages are observed in the process of setting of such cements. During the first stage the viscosity of the aqueous mix increases rapidly, but it may still be stirred, poured, cast or otherwise worked to give a desired shape to the finished product. This state terminates after a period $t_w$ known as the working time, when the mixture has achieved sufficient rigidity to prevent further working. During the second stage the material develops considerably greater mechanical strength until the setting time $t_s$, which is arbitrarily defined as the time at which the cement achieves a rigidity or strength appropriate to a particular use.

According to one aspect of the invention there is provided a partially or completely water soluble glass composition as hereinafter defined adapted to provide cross-linking of a polycarboxylic acid cement, said composition including a glass composition for effecting crosslinking of a polycarboxylic acid cement, said composition including an aluminoborate type glass, comprising 40 to 75 mole % boric oxide, not more than 20 mole % alumina, not more than 60 mole % zinc oxide, and not more than 50 mole % calcium oxide, the remainder if any comprising one or more further metal oxides, or phosphorus pentoxide or mixtures thereof.

According to another aspect of the invention there is provided a cement composition comprising a polycarboxylic acid material, and a partially or completely water soluble glass as hereinafter defined, said glass comprising a glass composition for effecting crosslinking of a polycarboxylic acid cement, said composition including an aluminoborate type glass, comprising 40 to 75 mole % boric oxide, not more than 20 mole % alumina, not more than 60 mole % zinc oxide, and not more than 50 mole % calcium oxide, the remainder if any comprising one or more further metal oxides, or phosphorus pentoxide or mixtures thereof.

The term "glass" as employed herein is understood to include not only homogeneous glass systems, but also partially devitrified and phase separated materials.

The term "polycarboxylic acid" as used herein is understood to include polymers of unsaturated monocarboxylic acids and their anhydrides or precursors thereof, unsaturated dicarboxylic acids and their anhydrides or precursors thereof, or copolymers formed from combinations thereof. Copolymers may also be formed from such materials together with other ethylenically unsaturated monomers. Specific monomers are acrylic, itaconic, mesaconic, citraconic or maleic acids or their respective anhydrides. The polycarboxylic acid may be in dry powder form or in aqueous solution.

We have found that within the aluminoborate glass system, certain compositions are particularly advantageous for effecting crosslinking of polycarboxylic acid cements. These compositions include zinc oxide and/or calcium oxide which oxides proved the necessary polyvalent metal ions to initiate the crosslinking reaction. In particular we have found that glasses in the composition range 40-75 mole % boric oxide ($B_2O_3$), not more than 60 mole % zinc oxide (ZnO) not more than 50 mole % calcium oxide (CaO) and not more than 20 mole % alumina ($Al_2O_3$) are particularly effective when employed with water setting polyacrylic acid (PAA) cements. The glasses may also contain small quantities of one or more alkali metal oxides, one or more alkaline earth metal oxides, one or more transition metal oxides, phosphorus pentoxide or mixtures thereof. The preferred alumina content of the glass composition is 4 to 7 mole % to provide convenient setting time of a PAA cement made from the glass.

We have also found that, within this glass composition range, glasses with a somewhat narrower composition range are particularly effective for crosslinking PAA cement. Thus, glasses within the preferred composition range contain 43 to 50 mole % boric oxide, 33-42 mole % calciumoxide, 11 to 14 mole % zinc oxide and 4 to 7 mole % alumina.

The glass compositions are prepared by fusing the constituent oxides, or compounds which on heating decompose to form the respective oxides, for a sufficient period of time to form an homogeneous melt. For example, one or more of the metal oxides may be replaced by the metal carbonate, acetate, citrate or mixtures thereof. This list is not exhaustive and other suitable organic acid salts may of course be employed. Typically, quantities of alumina and boric oxide, which latter acts as the glass forming oxide of the system, are fused together with zinc and calcium oxide, and optionally one or more further metal oxides at a temperature of 800° to 1,500° C. in an oxidising atmosphere. The one or more further metal oxides may act as crosslinking agents for polycarboxylic acid materials and for this purpose should comprise divalent or polyvalent metal oxides. To produce a desired glass composition it may be necessary to add an excess of boric oxide to the initial mix as some of this oxide may be lost by evaporation during the fusion process.

The molten glass is quenched to form a solid material which is then crushed and ground to fine powder, the degree of fineness depending on the particular application of the glass material. The exact composition of the glass may then be determined by chemical analysis of the powder.

The water solubility rate of the glass composition may be adjusted by incorporation of suitable further metal oxides. Thus, for example, calcium oxide reduces the solubility of the glass and also acts as a crosslinking agent for polycarboxylic acid materials. Other metals which may be incorporated by way of their oxides include magnesium, barium, strontium, copper, iron, nickel, cobalt or mixtures thereof. The glass may also incorporate one or more alkali metal oxides for the purpose of increasing water solubility.

The glass compositions may be employed in the preparation of polycarboxylic acid cements. Typically, weighed quantities of the powdered glass and the polycarboxylic acid, either in dry powder or aqueous solution form, are mixed together. Where the dry powders are employed sufficient water is added to initiate the crosslinking reaction. Setting of the cement generally proceeds in two stages during the first of which the material may be worked or moulded to the desired shape.

The preferred polymer materials for use with the glasses described herein are those based on acrylic acid. Thus, preferred homopolymers are acrylic acid or acrylic anhydride homopolymers. Acrylic acid copolymers preferably incorporate acrylamide or acrylonitrile as the ethylenically unsaturated monomer. Acrylic anhydride copolymers preferably incorporate ethylene, propylene, butane or styrene as the ethylenically unsaturated monomer. The number average molecular weight of the polymeric material may be from 1,000 to 1,000,000, materials within the range 1,000 to 500,000 being preferred.

In some applications, for example dental applications, it is advantageous to provide a dry pack mix of the glass and polycarboxylic acid, the cement being formed when required by adding a suitable quantity of water immediately prior to use. Thus, sufficient water may be added to form a thick paste which is injected into a tooth cavity and allowed to set. It is thought that the calcium ions present in the tooth interact with the polycarboxylic acid material and thus firmly bond the cement to the tooth.

In order to extend the setting times of cements formed with the glass compositions described herein, the glass may be subjected to one of the phosphate treatments described in our co-pending British application No. 43601/78 (C. F. Drake—N. R. Adams 66-1). In such a treatment glass particles are either coated with or used in conjunction with a phosphate material such as phosphoric acid, phosphorus pentoxide or an inorganic phosphate. The reaction mechanism is not fully understood, but the effect of such treatment is to extend the working time of the cement incorporating the glass without significantly extending the setting time of the cement. This of course greatly extends the range of glass compositions which may be employed and the range of applications for which cements incorporating such glasses may be used.

Typical therapeutic uses of cements formed from the glass compositions described herein include dental cements, orthopaedic cements, e.g. for splint bandages, and cements for the construction of prostheses such as are employed as human joint replacements. Other applications include but are not limited to structural cements which advantageously may be reinforced e.g. with glass, plastics, or carbon fibres, quick setting cements e.g. for emergency repairs to roads or aircraft runways, soil stabilization cements, vehicle body filler materials and grouting cements. In some applications the cements may contain chemically and/or biologically active materials. Thus a tile grouting cement may include a fungicide and/or a bacteriocide to prevent the growth of micro-organisms. Similarly, a vehicle body cement may include a metal corrosion inhibitor.

The glass composition may have various forms. Thus, the glass may comprise particles less than 250 microns, and preferably less than 75 microns in diameter. Alternatively the glass may be in fibre form either as separate fibres or as a woven or non woven fabric. Typically such fibres are less than 100 microns, and preferably less than 20 microns in diameter. Such fibres increase the strength of the cement composition.

In some applications the cement may also include organic or inorganic reinforcing fibres, and additives such as tartaric acid and sodium chloride which increase tensile strength and decrease shrinkage respectively.

In the cement composition described herein by weight ratio of glass:polymer is suitably from 0.5:1 to 5:1, and preferably from 1:1 to 3:1.

The particular composition range of the glass will of course depend on the particular combination of glass constituents. The glass forming regions and the preferred composition ranges have been determined for a number of glass systems and are summarized in the following Table.

TABLE 1

| System | Composition Ranges (mol %) | |
|---|---|---|
|  | Glass-forming | Preferred |
| $B_2O_3$ | 55–80 | 60–75 |
| CaO | 20–45 | 25–40 |
| $B_2O_3$ | 20–70 | 40–70 |
| $Al_2O_3$ | 0–30 | 0–10 |
| CaO | 15–50 | 20–40 |
| $B_2O_3$ | 35–50 | 45–50 |
| ZnO | 50–65 | 50–55 |
| $B_2O_3$ | 35–50 | 40–50 |
| $Al_2O_3$ | 0–15 | 0–10 |
| ZnO | 35–65 | 40–60 |
| $B_2O_3$ | 30–75 | 40–60 |
| $Al_2O_3$ | 0–20 | 0–10 |
| CaO | 0–50 | 20–40 |
| ZnO | 0–50 | 10–20 |

This latter system is particularly preferred for splinting cements.

The following Examples illustrate the invention.

EXAMPLE 1

A glass was prepared by fusing powders of $B_2O_3$, Al(OH)$_3$ and ZnO to a homogeneous melt of molar proportions.

$B_2O_3$—47.5
$Al_2O_3$—5.0
ZnO—47.5

The melt was quenched and milled to pass a sieve screen of aperture 38 μm. Samples were mixed intimately with powdered polyacrylic acid in the ratio of 3:1 by weight, and this powder was then stirred rapidly with half its weight of water to a smooth paste. After 13 seconds the paste became warm and gelled to a non-workable viscoelastic mass, and after 10 minutes it had set to a hard, water resistant solid with a tensile strength of 5.5 $GNm^{-2}$.

EXAMPLE 2

A glass was prepared by fusing powders of $B_2O_3$, Al(OH)$_3$, $CaCO_3$ and ZnO to a melt of molar proportions.

$B_2O_3$—46.5
$Al_2O_3$—6.0
CaO—35.0
ZnO—12.5

The melt was quenched, milled, subjected to an ammonium phosphate solution treatment as described in our co-pending Application No. 43601/78, and sieved to pass a screen of aperture 45 μm. Samples were mixed intimately with powdered PAA in the ratio 3:1 by weight, and this powder was stirred rapidly with half its weight of water to a smooth paste. After 40 seconds the paste gelled with little evolution of heat, and after 10 minutes had set to a tough elastic solid with high resistance to immersion in water.

EXAMPLE 3

A series of glass compositions was prepared by fusion of the constituent oxides. Melts were quenched and milled to pass a sieve screen of aperture 45 μm, and their working and setting times with powdered PAA were measured. In each case the glass was mixed with the PAA and water in the ratio 3:1:2.

The following table summarizes glass compositions and setting characteristics, where WT is the working time (i.e. time from mixing to gelation) in seconds. ST is the time to set (i.e. time from mixing to negligible penetration of a Gilmore needle) in minutes. Column 1 refers to untreated glass: column 2 refers to glass which has been subjected to a phosphate treatment as described in our co-pending British application No. 43601/78.

TABLE 2

| Composition (Mol %) | | | | | | | 1 | | 2 | |
|---|---|---|---|---|---|---|---|---|---|---|
| $B_2O_3$ | $Na_2O$ | MgO | $Al_2O_3$ | $P_2O_5$ | CaO | ZnO | WT | ST | WT | ST |
| 40.0 | 20.0 | — | 20.0 | — | 20.0 | — | 10 | 240 | | |
| 30.0 | 20.0 | — | 20.0 | — | 30.0 | — | 25 | 240 | | |
| 30.0 | 30.0 | — | 20.0 | — | 20.0 | — | 10 | 240 | | |
| 60.0 | 10.0 | — | 7.5 | — | 10.0 | 12.5 | 2 | 20 | 15 | 10 |
| 25.0 | 40.0 | — | 20.0 | — | 15.0 | — | 7 | 240 | 40 | 10 |
| 47.6 | 4.8 | — | 4.8 | — | 28.5 | 14.3 | 10 | 10 | 120 | 12 |
| 47.5 | — | 5.0 | 5.0 | — | — | 42.5 | 15 | 19 | | |
| 47.5 | — | 10.0 | 5.0 | — | — | 37.5 | 5 | 11 | | |
| 50.0 | — | 40.0 | 10.0 | — | — | — | 21 | 30 | | |
| 57.5 | — | 5.0 | — | — | 25.0 | 12.5 | 15 | 7 | 45 | 7 |
| 42.0 | — | 5.0 | 3.5 | — | 37.0 | 12.5 | 10 | 12 | 90 | 15 |
| 47.6 | — | — | 4.8 | 4.8 | 28.5 | 14.3 | 30 | 15 | 90 | 10 |
| 43.5 | — | — | 4.4 | 13.0 | 26.1 | 13.0 | 30 | 25 | | |
| 40.0 | — | — | 4.0 | 20.0 | 24.0 | 12.0 | 210 | 30 | | |
| 48.5 | — | — | 4.0 | — | 35.0 | 12.5 | 5 | 3 | 60 | 4 |
| 45.5 | — | — | 6.0 | — | 36.0 | 12.5 | 10 | 5 | 150 | 7 |
| 46.5 | — | — | 6.0 | — | 35.0 | 12.5 | 5 | 3 | 40 | 4 |
| 46.0 | — | — | 6.5 | — | 35.0 | 12.5 | 10 | 5 | 40 | 5 |
| 47.5 | — | — | 5.0 | — | 35.0 | 12.5 | 5 | 3 | 60 | 3 |
| 40.0 | — | — | 5.0 | — | 40.0 | 15.0 | 2 | 5 | 75 | 3 |
| 60.0 | — | — | 5.0 | — | 20.0 | 15.0 | 10 | 5 | 75 | 2 |
| 47.5 | — | — | 5.0 | — | 5.0 | 42.5 | 5 | 8 | | |
| 47.5 | — | — | 5.0 | — | 10.0 | 47.5 | 13 | 8 | | |
| 47.7 | — | — | 4.6 | — | 47.7 | — | 8 | 9 | | |
| 50.0 | — | — | — | — | — | 50.0 | 40 | 6.5 | | |
| 47.5 | — | — | 5.0 | — | — | 47.5 | 13 | 10 | 2 | 25 |
| 45.0 | — | — | 10.0 | — | — | 45.0 | 20 | 21 | | |
| 35.0 | — | — | — | — | — | 65.0 | 14 | 6 | | |

We claim:

1. A glass composition for effecting crosslinking of a polycarboxylic acid cement, said composition including an aluminoborate type glass comprising 40 to 75 mole % boric oxide, not more than 20 mole % alumina, not more than 60 mole % zinc oxide, and not more than 50 mole % calcium oxide, the remainder if any comprising one or more further metal oxides, or phosphorus pentoxide or mixtures thereof.

2. A glass composition for effecting crosslinking of a polycarboxylic acid cement, said composition including an aluminoborate type glass comprising 43 to 50 mole % boric oxide, 33 to 42 mole % calcium oxide, 11 to 14 mole % zinc oxide and 4 to 7 mole % alumina.

3. A glass as claimed in claim 1 or 2, in which further includes a minor proportion of one or more oxides of magnesium, barium, strontium, copper, iron, nickel, cobalt or mixtures thereof.

4. A glass as claimed in claim 1 which is in particulate form.

5. A glass as claimed in claim 4 in which said particles have a diameter less than 75 microns.

6. A glass as claimed in claim 1 which is in fibre form.

7. A glass as claimed in claim 6 in which said fibres comprise a woven or non-woven fabric.

* * * * *